United States Patent
Troup

(10) Patent No.: US 10,507,218 B2
(45) Date of Patent: Dec. 17, 2019

(54) TREATMENT OF CARDIOVASCULAR DISEASE BY USING GALLIUM COMPOUNDS TO BIND CALCIFIED LESIONS

(71) Applicant: LIPIDRISK, LLC, The Woodlands, TX (US)

(72) Inventor: Jan M. Troup, The Woodlands, TX (US)

(73) Assignee: LIPIDRISK, LLC, The Woodlands, TX (US)

( * ) Notice: Subject to any disclaimer, the term of this patent is extended or adjusted under 35 U.S.C. 154(b) by 0 days.

(21) Appl. No.: 16/281,518

(22) Filed: Feb. 21, 2019

(65) Prior Publication Data
US 2019/0255100 A1    Aug. 22, 2019

Related U.S. Application Data

(60) Provisional application No. 62/633,779, filed on Feb. 22, 2018.

(51) Int. Cl.
| | | |
|---|---|---|
| *A61K 33/24* | (2019.01) | |
| *A61P 19/00* | (2006.01) | |
| *A61P 19/02* | (2006.01) | |
| *A61K 9/00* | (2006.01) | |
| *A61K 9/70* | (2006.01) | |
| *A61P 7/00* | (2006.01) | |

(52) U.S. Cl.
CPC ............ *A61K 33/24* (2013.01); *A61K 9/0019* (2013.01); *A61K 9/0043* (2013.01); *A61K 9/0053* (2013.01); *A61K 9/7023* (2013.01); *A61P 7/00* (2018.01); *A61P 19/00* (2018.01); *A61P 19/02* (2018.01)

(58) Field of Classification Search
None
See application file for complete search history.

(56) References Cited

U.S. PATENT DOCUMENTS

| | | |
|---|---|---|
| 4,704,277 A | 11/1987 | Bockman |
| 5,175,006 A | 12/1992 | Matkovic |
| 5,196,412 A | 3/1993 | Bradley et al. |
| 5,700,487 A | 12/1997 | Gerber et al. |
| 6,203,822 B1 | 3/2001 | Schlesinger |
| 7,119,217 B2 | 10/2006 | Jiang |
| 7,354,952 B2 | 4/2008 | Julian |
| 8,168,214 B2 | 5/2012 | Bernstein |
| 9,205,108 B2 | 12/2015 | Troup |
| 2011/0104246 A1 | 5/2011 | Rogosnitzky |

OTHER PUBLICATIONS

Demer L, "Vascular calcification and osteoporosis: inflammatory responses to oxidized lipids" International Journal of Epidemiology, vol. 31, Issue 4, Aug. 1, 2002, pp. 737-741.
Warrell, R.P.; Brockman, R.S.; Coonley, C.J.; Isaacs, M. and Staszewski, H. Gallium nitrate inhibits calcium resorption from bone and is effective treatment for cancer-related hypercalcemia. I Clinical Investigation. 1984, 73, 1487-1490.
Todd, P.A. and Fitton, A. Gallium nitrate. A review of its pharmacological properties and therapeutic potential in cancer related hypercalcemia. Drugs. Aug. 1991, 42(2), 261-73.
Makkonen, M.-R, et al."The effect of free gallium and gallium in liposomes on cytokine and nitric oxide secretion from macrophage-like cells in vitro" Inflammation Research, 1995, vol. 44, pp. 523-528.
Bernstein "Mechanisms of Therapeutic Activity for Gallium" Pharmacological Reviews, 1998, vol. 50, No. 4, pp. 665-682.
Kritharides, L. et al "Coronary Uptake of Gallium-67 Citrate After Implantation of Sirolimus-Eluting Stent" Circulation, 2004, vol. 109, p. 2156.

*Primary Examiner* — Celeste A Roney
(74) *Attorney, Agent, or Firm* — Craft Chu PLLC; Andrew W. Chu

(57) ABSTRACT

The method for treating cardiovascular disease relates to stopping growth of an atherosclerotic plaque or lesion. A therapeutically effective amount of a pharmaceutically acceptable gallium compound is administered to an inflammation site in an artery with a lesion with microcalcifications. Gallium ions bind to the lesion. The proper amount of gallium compound delivered to the lesion disrupts a calcification process at the inflammation site. The gallium ions bind to calcium hydroxyapatites in microcalcifications so that the microcalcifications can no longer differentiate into early phase osteoblasts. The gallium integrated into the calcium structures at the inflammation site has a lasting effect to reduce atherosclerotic plaques.

19 Claims, 1 Drawing Sheet

GALLIUM IN MEDICAL TREATMENTS

| Condition | Cancer | Inflammation | Pain | Traumatic Brain Injury |
|---|---|---|---|---|
| Disruption in Calcification Process | x | | | |
| Inhibit macrophages of the inflammation response | | x | x | |
| Deliverable to calcium deposits | x | | | x |

TREATMENT OF CARDIOVASCULAR DISEASE BY USING GALLIUM COMPOUNDS TO BIND CALCIFIED LESIONS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to treatment of cardiovascular disease in mammals. More particularly, the present invention relates to treatment of atherosclerosis. The present invention also relates to treatments using gallium compounds to reduce inflammation of atherosclerotic lesions.

2. Description of Related Art Including Information Disclosed Under 37 CFR 1.97 and 37 CFR 1.98

Cardiovascular Disease is the leading cause of death in people of the United States. Cardiovascular disease relates to conditions of the heart and blood vessels. In particular, atherosclerosis can be an underlying condition related to narrowed arteries, which reduces the flow of blood. The heart works harder, and arteries are stressed. Atherosclerosis happens when plaque accumulates inside the arteries.

It is widely accepted that atherosclerosis develops from a macrophage scavenging of oxidized low density lipoproteins (LDLs) and oxidized or unoxidized remnant lipoproteins in the arterial intima to form foam cells in an initial lesion at an initial inflammatory response. The origin of this initial lesion is unknown, and there is no reliable detection of this initial lesion. It is known that growth of the initial lesion is fueled by lipoproteins. The inflammatory response has monocytes entering the artery wall from the bloodstream, and the monocytes mature into macrophages. Macrophages ingest LDLs and become foam cells. Thus, preventative treatments include eating a healthy diet and exercising regularly, which reduce the availability of LDLs.

The initial lesion grows as the foam cells are building blocks for an atherosclerotic lesion or plaque. More lipid uptake grows the initial lesion between the endothelial layer and the artery wall. In this stage, medications can be prescribed, such as statins, to lower the cholesterol levels or lipoprotein levels in the blood. Again, the treatment addresses the LDLs as fuel for growth of the lesion.

With the intermediate lesion, the inflammatory response also develops. There is now trauma to the cells of the endothelial layer and the smooth muscle cells adjacent to the intermediate lesion, which may become an atheroma due to continued growth by LDLs. A fibrous capsule can form due to the surrounding endothelial and muscle cells. This development of the inflammatory process also includes macrophages promoting the initial calcium deposition from foam cells in a process called micro-calcification. This mineralization differentiates into early phase osteoblasts, that produce hydroxyapatite, which resembles bone tissue. Calcification of the arteries and more specifically the coronary and carotid arteries is both an indicator and a contributor to atherosclerosis which leads to a life-threatening event for approximately 50% of the world's population. The fibers and calcium indicate a complicated lesion at more advanced stages of atherosclerosis.

Thus, late stage risk of atherosclerosis can be measured by looking at coronary calcification measured by techniques such as a coronary calcium score, carotid stenosis with a CIMT or Carotid Intima-Media Thickness or by measuring chronic inflammation with a C-reactive protein assay. A myocardial infarction also known as a cardiac event results from the rupture of an inflamed atherosclerotic lesion that is usually micro-calcified. A review of the development of vascular calcification and the inflammation process in atherosclerosis is discussed in Demer L, "Vascular calcification and osteoporosis: inflammatory responses to oxidized lipids" International Journal of Epidemiology, Volume 31, Issue 4, 1 Aug. 2002, Pages 737-741.

To date, no treatment for atherosclerosis has been found that stops or reduces, at the source, the inflammation in the calcified atherosclerotic lesion. Previous methods address the LDL availability to slow or prevent growth of the lesions. There is no disclosure for targeting an intermediate stage in the development of atherosclerosis. There is no disclosure or teaching that the calcium indicator is useful to treat atherosclerosis.

Gallium compounds are known effective drugs for reducing calcium levels in hypercalcemia patients and treating neuropathic pain, like N-type VGCC blockers. Gallium compounds have been studied for a variety of neurological aliments (Bernstein, U.S. Pat. No. 8,168,214). Gallium compounds are used to inhibit bone calcium loss (hypercalcemia) in cancer patients. See Warrell, R. P.; Brockman, R. S.; Coonley, C. J.; Isaacs, M. and Staszewski, H. Gallium nitrate inhibits calcium resorption from bone and is effective treatment for cancer-related hypercalcemia. I Clinical Investigation. 1984, 73, 1487-1490; and Todd, P. A. and Fitton, A. Gallium nitrate. A review of its pharmacological properties and therapeutic potential in cancer related hypercalcemia. Drugs. 1991, August, 42(2), 261-73 regarding use of gallium nitrate. Also, Bradley, et al., U.S. Pat. No. 5,196,412, describes compounds of gallium (III), which can be given orally to achieve high serum levels of gallium (III) for the treatment of hypercalcemia of malignancy and related disorders of bone metabolism.

Gallium compounds are known to both rapidly reduce edema in animals and humans. For example, Gerber et al., U.S. Pat. No. 5,700,487, discloses a method of treating pulmonary inflammation in mammals, comprising administering an effective amount of a pharmaceutically acceptable gallium compound and wherein said gallium is elected from the group consisting of gallium nitrate, gallium citrate, gallium chloride, gallium carbonate, gallium acetate, gallium tartrate, gallium oxalate, gallium oxide, gallium arsenide and hydrated gallium oxide.

Julian, U.S. Pat. No. 7,354,952, discloses novel pharmaceutical gallium compositions, including gallium complexes having increased oral bioavailability relative to uncomplexed gallium salts. Such compositions are useful in the treatment of conditions and diseases in which inhibition of abnormally increased calcium resorption is desired, including cancer, hypercalcemia, osteoporosis, osteopenia and Paget's disease.

Jiang et al., U.S. Pat. No. 7,119,217, incorporated herein by reference, discloses novel tri(alkylcarboxylato) gallium (III) compounds, exemplified by tripalmitato gallium (III), methods for making them, pharmaceutical compositions containing them, and methods of using the pharmaceutical compositions. These compounds may be useful especially since a DHA is a member of this family of compounds.

Gallium compounds are known treatment in humans for cancer and pain. U.S. Pat. No. 4,704,277 shows that doses of 100-300 mg/sq mm m/day of gallium nitrate over 5-7 days reduce calcium excretion by 70+18%. In the cancer treatments, the gallium appears to inhibit calcium resorption from bone and the exact mechanism is unknown although it could be a reaction with the calcium apatite bone structure binding the calcium into a harder bone structure.

Gallium nitrate is a particular gallium compound. Gallium nitrate is known to treat mammals for pain and anti-bacterial agents. Matkovic et al., U.S. Pat. No. 5,175,006 discloses inflammation pain treatment, and Gerber et al., U.S. Pat. No. 5,700,487, describes pulmonary inflammation treatment in humans and animals. Gallium compounds are also powerful antibacterial and anti-pathogenic agents as taught by Schlesinger et al., U.S. Pat. No. 6,203,822, which further discloses the use of gallium-containing compounds to inhibit intracellular pathogens including pathogens that are members of the genus *Mycobacteria, Legionella, Histoplasma*, and *Leishmania* and to organisms causing chronic pulmonary infection such *P. aeruginosa*. Additionally, gallium nitrate has been shown to be an effective for wound treatment as taught by Rogosnitzky, U.S. Pat. App. Pub. No. 20110104246, as a pharmaceutical composition and method for topical wound treatment by topical treatment with gallium salts, preferably gallium nitrate.

Gallium therapy to treat concussion or traumatic brain injury has been shown by Troup, U.S. Pat. No. 9,205,108B2 in animal studies by the reduction of carbonyl oxidation and protein nitration. The nitration reduction is remarkable since the therapy used the non-steroid gallium nitrate, a powerful oxidizing agent. The therapy is based on a three-fold approach where gallium compounds reduce serum calcium levels that cause much of the damage in a traumatic brain injury, as an N-type voltage-gated calcium channel neuropathic pain blocker and finally as a powerful anti-inflammatory agent.

Gallium compounds have also been found to inhibit dose-dependent secretion of IL-6, TNF alpha and NO from activated macrophages. See Makkonen, M.-R, et al. "The effect of free gallium and gallium in liposomes on cytokine and nitric oxide secretion from macrophage-like cells in vitro" Inflammation Research, 1995, vol. 44, pp. 523-528. FIG. 1 summarizes the prior art based on Bernstein "Mechanisms of Therapeutic Activity for Gallium" Pharmacological Reviews, 1998, vol. 50, No. 4, pp. 665-682 and Kritharides, L. et al "Coronary Uptake of Gallium-67 Citrate After Implantation of Sirolimus-Eluting Stent" Circulation, 2004, vol. 109, p. 2156.

It is an object of the present invention to provide a treatment for cardiovascular disease.

It is another object of the present invention to provide a treatment for cardiovascular disease with a gallium compound.

It is still another object of the present invention to provide a treatment for cardiovascular disease with a gallium compound to bind calcified lesion structures.

It is still another object of the present invention to provide a treatment for cardiovascular disease to bind calcified lesions by incorporating gallium ions into the calcium hydroxyapatite structure.

These and other objects and advantages of the present invention will become apparent from a reading of the attached specification and appended claims.

BRIEF SUMMARY OF THE INVENTION

Cardiovascular disease is characterized by atherosclerosis. An initial lesion in an artery triggers an initial inflammatory response. The availability of cholesterols, including LDLs, spurs growth of the lesion, which further complicates the inflammatory response. The later inflammatory response includes micro-calcification, which further grows and transforms the lesion into a complex fibroatheroma with fibrotic and calcific layers. Thus, the elevated level of calcium at the site of the lesion as part of an inflammatory response is a metric of atherosclerosis. Even if known to affect calcium levels for bone loss in cancer patients and edemas in pulmonary inflammation, the present invention discloses gallium compounds to disrupt the calcification process at the site of the initial lesion in the artery.

The present invention is a method for treating cardiovascular disease in a mammal by administering a therapeutically effective amount of a pharmaceutically acceptable gallium compound to an arterial inflammation site with a lesion being comprised of microcalcifications. The proper amount of the gallium compound delivered to the site with the lesion disrupts the further calcification process by M1 macrophages. The microcalcifications can no longer differentiate into early phase osteoblasts comprised of calcium hydroxyapatites so that the lesion cannot grow into the more complicated and dangerous lesions of atherosclerosis. The gallium compound remains at the site for a lasting effect on the lesion.

DETAILED DESCRIPTION OF THE INVENTION

Figures 1, 2:
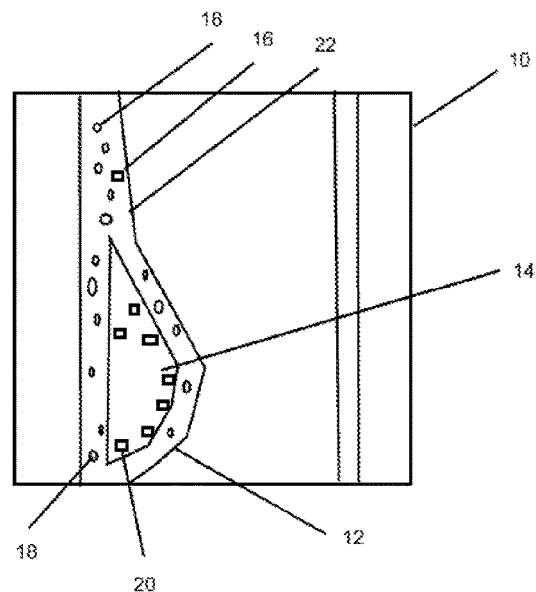
FIG. 1 is a chart summary of treatments with gallium.
FIG. 2 is a schematic illustration of an arterial inflammation site with a lesion comprised of microcalcifications.

Convention treatment of cardiovascular disease relates to reducing the availability of cholesterol, such as LDLs, so as to restrict growth of the lesion in the artery. Treatments at an early stage of atherosclerosis include eating a healthy diet and exercising to address the LDLs as the food or fuel of growing lesions. Treatment with medications also focus on the reduced consumption of LDLs by the cellular components of the initial lesion, such as monocytes, macrophages, and eventual foam cells. Instead of targeting LDLs from the initial lesion at the initial inflammation site 12 in the artery 10, a method of treatment in FIG. 2 may disrupt an intermediate process to prevent the growth and complication of the initial lesion 14 into the advanced and critical stages of atherosclerosis. The present invention discloses a treatment method for this process to prevent an intermediate lesion from further development to the more critical stages.

Gallium compounds have been shown to have a very high affinity for osteoblast cells, particularly when inflamed, and other calcium hydroxyapatite structures. Gallium compounds have also been shown to be highly effective anti-inflammatory agents. In the present invention, gallium compounds are the therapeutic agent to treat an arterial inflammation site with a lesion being comprised of microcalcifications. The availability and management of LDLs are not related to the therapeutic treatment of the present invention. The method of the present invention provides ease of application of gallium compounds and the longevity of the treatment.

The method for treating cardiovascular disease in a mammal comprises the step of administering a therapeutically effective amount of a pharmaceutically acceptable gallium compound to an arterial inflammation site 12 in the artery 10 of the mammal. An atherosclerotic lesion 14 with microcalcifications 20 is at the arterial inflammation site so as to bind gallium ions into the calcium hydroxyapatite structure of the lesion. At the inflammation site in the artery, M1 macrophages 18 release IL-1beta, IL-6, IL-12 and TNF alpha to promote the initial calcium deposition 16 within the lesion. Gallium ions delivered to the inflammation site incorporate into or bind to the calcium apatite structure of the lesion to stop growth of the lesion.

Less inflammation is an indicator of the gallium ions bonding to the calcium structures of the lesion, according to the present invention. When bonded to the calcified lesion structure, the calcified lesion stops growing. Thus, there is no additional trauma at the arterial inflammation site and adjacent cells 22 to the inflammation site. The normal inflammation response includes calcification to build the plaque, which affects additional arterial cells. Those newly affected arterial cells 22 would trigger a new round of the conventional inflammatory response with more monocytes, macrophages, and subsequent foam cells. The gallium ions block new initial lesions on healthy cells adjacent to the initial arterial inflammation site.

The gallium compound of the present invention is disclosed. The action of the gallium compound is two-fold since gallium compounds are known to reduce hypercalcemia (bone calcium and calcified arthritic lesions) in patients and also have been shown to reduce edema in animals and humans. Safe and effective amounts of gallium compounds have been approved for treatment in the past. The gallium compound is selected from a group consisting of: gallium nitrate, gallium citrate, gallium chloride, gallium fluoride, gallium phosphate, gallium carbonate, gallium acetate, gallium tartrate, gallium oxalate, gallium formate, gallium oxide, gallium sulfate, gallium arsenide, gallium maltolate, gallium 8-quinolinolate and hydrated gallium oxide, gallium pyridinones, gallium succinate, gallium gluconate, gallium 3-hydroxy-4-pyrone, gallium palmitrate, the tridocosahexaenoic acid salt of gallium, or other tri(alkylcarboxylato) gallium (III) compounds, and combinations thereof. In particular, gallium nitrate and a docosahexaenoic acid salt of gallium, have been disclosed for hypercalcemia and/or related to the docosahexaenoic acid (DHA), the current treatment for concussion. The docosahexaenonic acid salt of gallium is a fatty acid triglyceride salt with known combination to one to three DHA molecules, also being fats.

The step of administering includes delivery to the arterial inflammation site with the atherosclerotic lesion in known vectors, including orally, by injection, intravenously, subcutaneously, transdermally, intramuscularly, and by inhalation. Injection includes intravenous, subcutaneous, and intraperitoneal injection. Transdermal delivery includes patches, passive transdermal single-layer technology, multi-layer drug-in-adhesive technology, and microneedle systems. Inhalation includes delivery by nasal spray or oral spray. In some embodiments, orally, transdermally, and nasal inhalation are supplied in a first aid kit.

The gallium compound with or without a citrate (such as in the Ganite formulation) should be administered in a sufficient amount, with 200 mg/m2 or approximately 4 mg/kg of body weight for 1-7 days as the initial dose. This effective amount is within the standard FDA approved doses of gallium compound for other conditions.

The present method includes repeating the step of administering. Follow up treatments from one month to every several years may be necessary to maintain the binding to the calcified structures of the lesion, depending the activity and stage of the atherosclerosis. The method of the present invention can be concurrent with standard treatments for atherosclerosis related to LDL and cholesterol availability, such as statins, absorption inhibitors, PCSK9 inhibitors, niacin, omega-3's or other therapies, depending on the activity of the atherosclerosis and the history of the patient.

Although gallium nitrate is the most common form of gallium for various treatments other salts or complexes of gallium may be found to be absorbed more rapidly or may be more specific for reducing hypercalcemia and/or inflammation.

From the observed extended anti-inflammatory activity of gallium compounds in animals and humans, the treatment for atherosclerosis may only need to be applied every few years to provide protection.

Furthermore, with regard to atherosclerotic plaque treatment of the present application, it is often difficult to diagnosis atherosclerosis, especially in younger patients. Diagnostic methods, such as lipoprotein particle analysis to measure the atherogenic particles of VLDL-P, RLP-P, LDL I-P, LDL II-P, LDL III-P, LDL IV-P and the cardioprotective particles such as HDL-P subgroups and especially HDL3-P are useful risk indicators. Additionally, Apo B-100 as a measure of all atherogenic particles is helpful in determining risk. Since most of LDL must be oxidized, except for lipoprotein remnants, to be taken up by macrophage cells to form plaque, a measurement of the oxidative susceptibility of LDL is a useful risk indicator as described by Troup et al. WO2016/049528A1. Chronic inflammation, a necessary component for plaque formation by the calcification process can be measured by a C-reactive protein assay and cytokines such as IL-1beta, IL-6, IL-12 and TNF alpha. These methods give an early stage indication of atherosclerotic risk, plaque development and calcification. Later stage calcification can be followed directly with a Coronary Calcium Score or Carotid Intima-Media Thickness measurement.

Patients with an early high-risk determination, later stage direct determination of calcified plaque formation or known cardiovascular disease that can lead to rupture and ischemic stroke or myocardial infarction, are possible candidates for gallium therapy to stabilized venerable plaque. A gallium nitrate dose of 0.5 to 20.0 mg/kg/day of body weight should be applied or 200 mg/m2/day being the preferred FDA dose.

Gallium therapy is rapidly absorbed through the skin in a trans-dermal application or can be administered orally, by spray, intravenously, subcutaneously, intramuscularly, or through oral or nasal inhalation. Other gallium compounds may also provide similar anti-inflammatory properties. The above dose should be applied for 1 to 7 days initially with follow up treatments provided in 1 to 120 months.

The gallium treatment effectiveness can be followed by measuring the inflammation marker C-reactive protein and other inflammation markers or by direct measurement of coronary calcium score, CIMT and other imaging technologies.

GALLIUM TREATMENT EXAMPLES

Example 1: Treatment of Plantar Fasciitis

The patient was having continuous severe pain from the plantar fasciitis for over six months after treatments with injected cortisone, special braces and hydrotherapy none of which gave relief.

Patient was treated with 5 ml's of 14% gallium nitrate solution applied to the bottom of the affected foot for 30 minutes every other day for three treatments. After each treatment the remaining solution was washed off and the exact amount of absorbed gallium nitrate was not measured. Patient noticed complete relief of pain for several hours after each treatment with the pain returning to a lesser extent 24 hours later. After the third treatment much of the pain was gone and the pain disappeared completely one week later. The plantar fasciitis has not returned for 10 years. The pain elimination from reduced inflammation is an indicator that the gallium ions bonded to the calcified structures at an inflammation site.

Example 2: Treatment of Arthritis of the Wrist

Patient had persistent rheumatoid arthritis of the wrist for over six months and was treated with a single dose of ¾ ml of 14% gallium nitrate solution, about 100 mg, as a topical application for one hour. Some pain relief was noticed immediately and after two months the arthritic pain was not noticeable. Patient has not experienced arthritic pain in the wrist for two years. Again, the pain elimination from reduced inflammation is an indicator that the gallium ions bonded to the calcified structures at an inflammation site.

The present invention provides a treatment for cardiovascular disease with a gallium compound. Other medical conditions have been treated with gallium compounds, including hypercalcemia in cancer patients and pulmonary edemas. For cardiovascular disease, the inflammation sites in the arteries are difficult to isolate for effective and long-lasting treatment. Conventional treatment of inflammation cannot remain at inflammation sites in the cardiovascular system. As shown in FIG. 1, the previously known medical treatments have identified the affinity for calcium in cancer and traumatic brain injury, while the pain and inflammation treatments do not track to particular locations. The basis of FIG. 1 establishes the connection between arterial sites and gallium concentrations at the arterial sites. A gallium scan is a more conventional scan given to a cancer patient, so that the lymphomas can be identified. However, the gallium scan given to a patent without lymphoma revealed the location of calcium deposits in the arteries. When there is no larger calcium burst (TBI, lymphoma), the remaining calcium deposits are the arterial inflammation site corresponding to cardiovascular disease.

The present invention makes the connections beyond the prior art findings of FIG. 1. The calcium deposits and microcalcifications in initial lesions and complicated lesions can also isolate gallium ions to those arterial inflammation sites. The present invention provides a treatment that can stop the calcification process in a lesion at an arterial inflammation site and remain active at that site in the arteries for significant reduction of cardiovascular disease. The present invention provides a treatment with an anti-inflammatory effect sustained at the arterial inflammation site, including preventative effects on adjacent cells. The inflammatory response does not spread. The present invention relies on the known affinity of gallium for bone calcium, present in cancer treatments with gallium compounds, and the calcification process in plaque formation to target the initial arterial inflammation sites. The macrophages responsible for the microcalcification are shown to have reduced macrophage cytokines, in particular, IL-1beta and LI-6, when treated with gallium. These same macrophage cytokines are the most common in atherosclerosis. In the present invention, a gallium compound attracts to the calcium in calcified lesion structures, triggered by M1 macrophages in response to the initial arterial inflammation. Gallium ions are incorporated into the calcium hydroxyapatite structure at the arterial inflammation site and remain at the inflammation site to prevent continued plaque growth. The lesion does not grow, no adjacent arterial cells trigger another round of the inflammatory response. Thus, initial inflammation sites in arteries can be specifically targeted and bound for long periods of time for the effective treatment of cardiovascular disease.

Additionally, the benefit of rapid and long-lasting anti-inflammation action makes gallium compounds a unique composition to prevent the growth of an atherosclerotic lesion or plaque. Gallium treatment does not appear to suppress the immune system, like other anti-inflammatory agents such as steroids. Additionally, other anti-inflammatory materials are not chemically attracted to the calcified plaque structures like in the present gallium therapy.

The foregoing disclosure and description of the invention is illustrative and explanatory thereof. Various changes in the details of the described method can be made without departing from the true spirit of the invention.

I claim:

1. A method of treating cardiovascular disease in a mammalian individual, said method comprising the steps of:
administering a therapeutically effective amount of a pharmaceutically acceptable gallium compound to an arterial inflammation site with a lesion being comprised of microcalcifications so as to bind gallium ions to said lesion.

2. The method of treating cardiovascular disease, according to claim 1, further comprising the step of:
binding gallium ions to calcium hydroxyapatites at said arterial inflammation site.

3. The method of treating cardiovascular disease, according to claim 1, further comprising the step of:
reducing osteoblasts at said arterial inflammation site.

4. The method of treating cardiovascular disease, according to claim 1, wherein said gallium compound is selected from a group consisting of: gallium nitrate, gallium citrate, gallium chloride, gallium fluoride, gallium phosphate, gallium carbonate, gallium acetate, gallium tartrate, gallium oxalate, gallium formate, gallium oxide, gallium sulfate, gallium arsenide, gallium maltolate, gallium 8-quinolinolate and hydrated gallium oxide, gallium pyridinones, gallium succinate, gallium gluconate, gallium 3-hydroxy-4-pyrone, gallium palmitrate, the tridocosahexaenonic acid salt of gallium, or other tri(alkylcarboxylato) gallium (III) compounds, gallium prophyrins, gallium transferrins, gallium pyridoxal isonicotinoyl hydrazine, and combinations thereof.

5. The method of treating cardiovascular disease, according to claim 1, wherein said gallium compound is administered orally.

6. The method of treating cardiovascular disease, according to claim 1, wherein said gallium compound is administered by injection.

7. The method of treating cardiovascular disease, according to claim 1, wherein said gallium compound is administered by intraperitoneal injection.

8. The method of treating cardiovascular disease, according to claim 1, wherein said gallium compound is administered by transdermal patch.

9. The method of treating cardiovascular disease, according to claim 1, wherein said gallium compound is administered by nasal spray.

10. The method of treating cardiovascular disease, according to claim 1, further comprising the steps of:
administering another therapeutically effective amount of said pharmaceutically acceptable gallium compound to said arterial inflammation site with said lesion so as to continue binding said gallium ions to said lesion.

11. A method of treating cardiovascular disease in a mammalian individual, said method comprising the steps of:
administering a therapeutically effective amount of a pharmaceutically acceptable gallium compound to an arterial inflammation site with a lesion being comprised of microcalcifications so as to stop a calcification process of said lesion.

12. The method of treating cardiovascular disease, according to claim 11, further comprising the step of:
binding gallium ions to calcium hydroxyapatites at said arterial inflammation site.

13. The method of treating cardiovascular disease, according to claim 11, further comprising the step of:
reducing osteoblasts at said arterial inflammation site.

14. The method of treating cardiovascular disease, according to claim 11, further comprising the steps of:
administering another therapeutically effective amount of said pharmaceutically acceptable gallium compound to said arterial inflammation site with said lesion so as to continue stopping said calcification process of said lesion.

15. The method of treating cardiovascular disease, according to claim 11, wherein said gallium compound is selected from a group consisting of: gallium nitrate, gallium citrate, gallium chloride, gallium fluoride, gallium phosphate, gallium carbonate, gallium acetate, gallium tartrate, gallium oxalate, gallium formate, gallium oxide, gallium sulfate, gallium arsenide, gallium maltolate, gallium 8-quinolinolate and hydrated gallium oxide, gallium pyridinones, gallium succinate, gallium gluconate, gallium 3-hydroxy-4-pyrone, gallium palmitrate, the tridocosahexaenonic acid salt of gallium, or other tri(alkylcarboxylato) gallium (III) compounds, gallium prophyrins, gallium transferrins, gallium pyridoxal isonicotinoyl hydrazine, and combinations thereof.

16. The method of treating cardiovascular disease, according to claim 11, wherein said gallium compound is administered orally.

17. The method of treating cardiovascular disease, according to claim 11, wherein said gallium compound is administered by injection.

18. The method of treating cardiovascular disease, according to claim 11, wherein said gallium compound is administered by transdermal patch.

19. The method of treating cardiovascular disease, according to claim 11, wherein said gallium compound is administered by nasal spray.

* * * * *